United States Patent [19]

Ackerman

[11] 4,031,088

[45] June 21, 1977

[54] IODINATED ANILIC ACIDS

[75] Inventor: James H. Ackerman, Bethlehem, N.Y.

[73] Assignee: Sterling Drug Inc., New York, N.Y.

[22] Filed: June 10, 1974

[21] Appl. No.: 478,052

Related U.S. Application Data

[60] Division of Ser. No. 323,710, Jan. 15, 1973, abandoned, which is a division of Ser. No. 109,631, Jan. 25, 1971, Pat. No. 3,770,820, which is a division of Ser. No. 25,262, April 2, 1970, Pat. No. 3,666,760, which is a continuation-in-part of Ser. No. 808,653, March 19, 1969, Pat. No. 3,609,147, which is a continuation-in-part of Ser. No. 715,558, March 25, 1968, abandoned, which is a continuation-in-part of Ser. No. 550,614, May 17, 1966, abandoned, said Ser. No. 808,653, is a continuation-in-part of Ser. No. 715,583, March 25, 1968, abandoned.

[52] U.S. Cl. .................. 260/247.2 A; 260/243 B; 260/244 R; 260/281 GN; 260/293.77; 260/326.4; 260/326.44; 260/404; 260/471 A; 260/518 A
[51] Int. Cl.$^2$ ..................................... C07D 295/00
[58] Field of Search .................. 260/247.2 A, 326.4, 260/293.77

[56] References Cited

FOREIGN PATENTS OR APPLICATIONS 274,795   9/1969   Austria

*Primary Examiner*—Paul J. Killos
*Attorney, Agent, or Firm*—Thomas J. Johnson; B. Woodrow Wyatt

[57] ABSTRACT

3-Amino-2,4,6-triiodobenzoic acids optionally substituted in the 5-position by amino or carboxy or a derivative thereof react with dibasic acid anhydrides to give the corresponding cyclic imides (A), which can be hydrolyzed to the corresponding anilic acids (B). The latter can be further alkylated on the anilide nitrogen atom. Compounds A and B are useful as cholecystographic and urographic agents.

5 Claims, No Drawings

IODINATED ANILIC ACIDS

This application is a division of my prior copending application, Ser. No. 323,710, filed Jan. 15, 1973, now abandoned, which is in turn a division of my prior copending application, Ser. No. 109,631, filed Jan. 25, 1971, now U.S. Pat. No. 3,770,820, which is in turn a division of my prior application, Ser. No. 25,262, filed Apr. 2, 1970, now U.S. Pat. No. 3,666,760, which is in turn a continuation-in-part of my prior copending application, Ser. No. 808,653, filed Mar. 19, 1969, now U.S. Pat. No. 3,609,147, which is in turn a continuation-in-part of my prior application, Ser. No. 715,558, filed Mar. 25, 1968, now abandoned, which is in turn a continuation-in-part of my application, Ser. No. 550,614, filed May 17, 1966, now abandoned. Application Ser. No. 808,653 is also a continuation-in-part of my prior application, Ser. No. 715,583, filed Mar. 25, 1968, now abandoned.

This invention relates to iodinated aniline derivatives and their preparation, and more particularly is concerned with iodinated benzene cyclic imide derivatives and the corresponding anilic acids, with intermediates therefor, and with methods for their preparation.

A preferred aspect of the invention resides in compounds of the formulas:

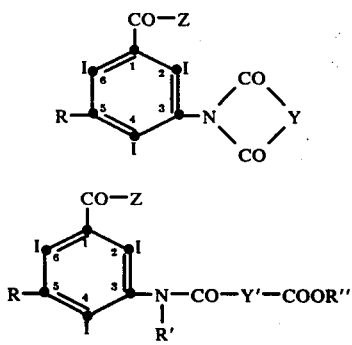

wherein Y is a lower-alkylene group wherein 2 or 3 carbon atoms separate the carbonyl groups, vinylene, or a 1,3-propylene group wherein the 2-carbon atom is replaced by O. S. SO or $SO_2$; Y' is a single bond, vinylene, or an alkylene bridge having from one to eight carbon atoms or such a group interrupted by from one to three members selected from O, S, SO and $SO_2$, said members, when more than one, being separated by at least two carbon atoms, Z is OH, O-lower-alkyl, lower-alkyl, phenyl, $NH_2$, NH(lower-alkyl), N(lower-alkyl)$_2$, morpholino, pyrrolidino or piperidino; R is $H_2N$,

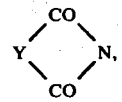

HOOC—Y'—CO—NH, HOOC—Y'—CO—N(lower-alkyl), T—CO—NH, T—CO—NHCH$_2$, or (T—CO)N(lower-alkyl), where T is hydrogen, cycloalkyl of 3–6 ring members, or alkyl of 1–8 carbon atoms optionally interrupted by from 1 to 4 oxygen atoms, each oxygen, when more than one, being separated by at least two carbon atoms; R' is hydrogen, lower-alkyl, hydroxy-lower-alkyl, lower-alkoxy-lower-alkyl, or lower-alkoxy-loweralkoxy-lower-alkyl; and R" is hydrogen or lower-alkyl.

In the above formulas A and B, Y stands, inter alia, for a lower-alkylene group wherein 2 or 3 carbon atoms separate the carbonyl groups and thus can be an ethylene or propylene group optionally substituted by lower-alkyl. The group Y can have from two to six carbon atoms and includes such groups as —CH$_2$CH$_2$—, —CH$_2$CH$_2$CH$_2$—, —CH(CH$_3$)CH$_2$—, —CH$_2$CH(CH$_3$)CH$_2$—, —CH(CH$_3$)CH(CH$_3$)—, —CH$_2$CH(C$_2$H$_5$)CH$_2$—, —CH(CH$_3$)CH$_2$CH$_2$—, —CH(CH$_3$)CH(CH$_3$)CH(CH$_3$)—, —CH$_2$C(CH$_3$)$_2$CH$_2$—, and the like. Y also stands for a 2-oxa- or 2-thia-1,3-propylene group having from 2 to 4 carbon atoms, for example, —CH$_2$OCH$_2$—, —CH$_2$SCH$_2$—, —CH$_2$SOCH$_2$—, —CH$_2$SO$_2$CH$_2$—, —CH(CH$_3$)OCH(CH$_3$)—, and the like. The group Y' in formula B is not limited to a two or three carbon bridge but may have up to eight carbons separating the carbonyl and carboxyl groups.

In the above formulas A and B, when Z stands for O-lower-alkyl, lower-alkyl, NH(lower-alkyl) or N(lower-alkyl)$_2$, and/or R stands for HOOC-Y'-CO-N(lower-alkyl) or (T-CO)N(lower-alkyl), and/or R' stands for lower-alkyl, lower-alkoxy-lower-alkyl, or lower-alkoxy-lower-alkoxy-lower alkyl, and/or R" stands for lower-alkyl, the lower-alkyl and lower-alkoxy groups have from one to six carbon atoms, thus including, for example, methyl, methoxy, ethyl, ethoxy, propyl, isopropyl, butyl, butyloxy, isobutyl, pentyl, hexyl and hexyloxy.

In the foregoing definitions, where T stands for cycloalkyl of 3–6 ring members, the cycloalkyl thus includes cyclopropyl, cyclobutyl, cyclopentyl, cyclohexyl, and lower-alkylated derivatives thereof, for example, 2-methylcyclopropyl, 3-ethylcyclopentyl, 3,4-dimethylcyclohexyl, and the like.

The method of preparation of the compounds of formulas A and B varies according to the structure desired as follows:

1. Compounds of formula A where R is

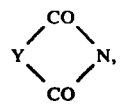

HOOC-Y-CO-N(lower-alkyl), T-CO-NHCH$_2$ or (T-CO)N(lower-alkyl).

a. Using a dibasic acid anhydride:
A compound of the formula

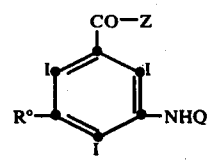

wherein R° is

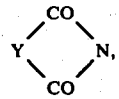

HOOC-Y-CO-N(lower alkyl), T-CO-NH, T-CO-NHCH$_2$, or (T-CO)N(lower-alkyl), Z, T and Y having the same meanings given hereinabove, and Q is hydrogen or lower-alkanoyl, is heated with an acid anhydride of the formula

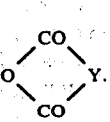

When Y is a lower-alkylene group, the reaction is preferably carried out in the presence of a strong acid catalyst, for example, sulfuric acid or phosphoric acid. When the reaction is carried out with a compound of formula C wherein Q is lower-alkanoyl, the lower-alkanoyl group is lost and replaced by the cyclic imide group.

b. Using a succinyl or glutaryl chloride:

A compound of formula C where Q is hydrogen is heated with a compound of the formula Cl-OC-Y-CO-Cl, where Y is a lower-alkylene group wherein 2 or 3 carbon atoms separate the carbonyl groups, in an inert solvent.

2. Compounds of formula B where R' is hydrogen.

a. Where Y' is within the scope of Y, and R" is hydrogen:

These compounds can be prepared by alkaline hydrolysis of the corresponding compounds of formula A. The reaction takes place in aqueous solution under mild conditions, at room temperature.

b. Where R is as given under method (1) above:

These compounds can be prepared by reacting a compound of formula C where Q is hydrogen with a half ester half acid chloride, Cl-CO-Y'-CO-OR", in an inert solvent, affording a compound of formula B where R" is lower-alkyl. Hydrolysis of the latter under mild alkaline conditions gives an anilic acid of formula B where R" is hydrogen.

3. Compounds of formulas A and B wherein R is $NH_2$ or T-CO-NH.

These compounds can be prepared from 3-amino-5-nitrobenzoic acid or an ester or amide thereof according to the following flow sheet (Z and Y having the meanings given hereinabove):

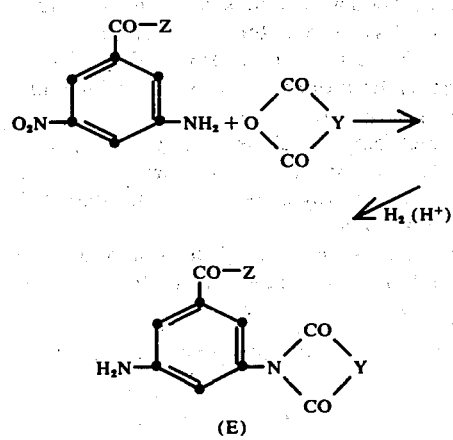

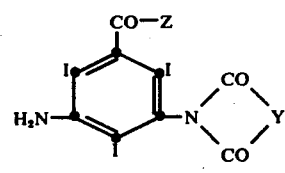

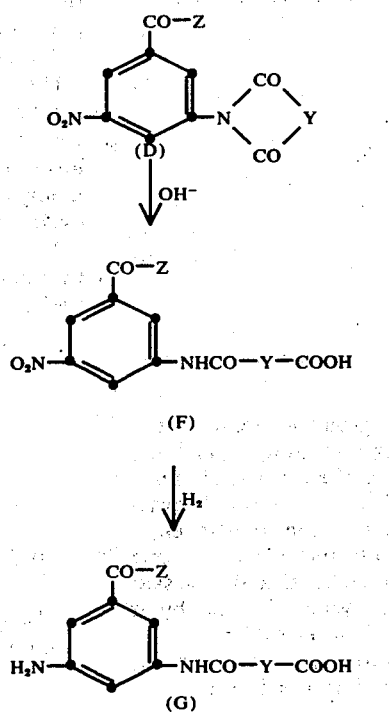

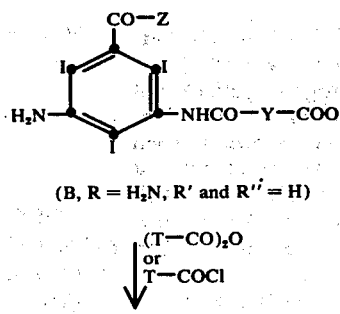

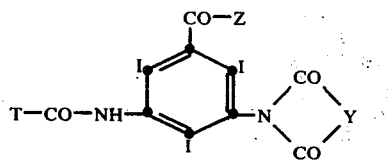
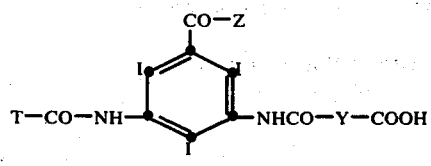

3-Amino-5-nitrobenzoic acid or an amide or ester thereof is reacted with an anhydride, O(CO)₂Y, to give the cyclic imide (D). The latter can either be hydrogenated under acid or neutral conditions to give the amino cyclic imide (E) or hydrolyzed under basic conditions to give the corresponding nitro-anilic acid (F). The nitro-anilic acid in turn can be hydrogenated to the amino-anilic acid (G). Iodination of the amino cyclic imide (E) affords a compound of formula A where R is H₂N, and iodination of the amino-anilic acid (G) gives a compound of formula B where R is H₂N and R' is H. The primary amino groups can then, if desired, be acylated with an acid anhydride or acid chloride to give, respectively, a compound of formula A where R is T-CO-NH, or a compound of formula B where R is T-CO-NH and R' is hydrogen.

4. Compounds of formulas A and B where the groups in the 3- and 5-positions are identical.

These are most conveniently prepared from 3,5-diamino-2,4,6-triiodobenzoic acid, or an ester or amide thereof. The latter is reacted with at least two equivalents of an anhydride, O(CO)₂Y, to afford a compound of formula A where R is Y(CO)₂N, which then can be hydrolyzed to a compound of formula B where R is HOOC-Y-CONH and R' is H. The starting material can also consist of a 3-lower-alkanoylamino-5-amino-2,4,6-triiodobenzoic acid or a 3,5-bis(lower-alkanoylamino)-benzoic acid. In the reaction with the anhydride the lower-alkanoyl groups are replaced by cyclic imide groups. Alternatively, a method analogous to method 2(b) above can be used, for example, reacting 3,5-diamino-2,4,6-triiodobenzoic acid with a half ester half acid chloride Cl-CO-Y'-CO-OR", affording a compound of formula B where R is R"OCO-Y'-CONH, R' is H and R" is lower-alkyl.

5. Compounds of formula B wherein R' is lower-alkyl, hydroxy-lower-alkyl, lower-alkoxy-lower-alkyl or lower-alkoxy-lower-alkoxy-lower-alkyl.

These compounds can be prepared by N-alkylation of the corresponding compounds where R' is hydrogen. The alkylation is effected by the action of R' halide, R' sulfate, R' alkylsulfonate or R' arylsulfonate in the presence of aqueous alkali, wherein R' is lower-alkyl, hydroxy-lower-alkyl, lower-alkoxy-lower-alkyl or lower-alkoxy-lower-alkoxy-lower-alkyl. If the starting material is a compound of formula B where R is T—CO—NH or HOOC—Y'—CO—NH, alkylation occurs on both nitrogens simultaneously.

6. Compounds of formulas A and B wherein R is (T-CO)N(lower-alkyl).

An alternative synthesis of these compounds is outlined in the following flow sheet:

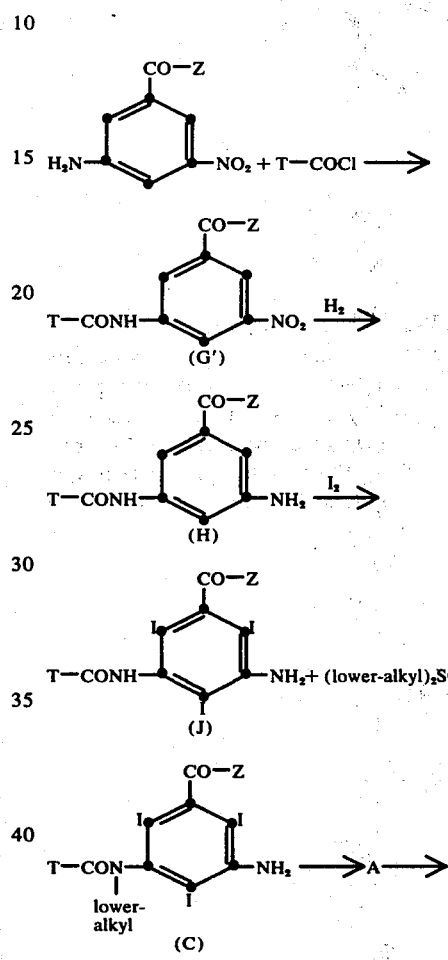

In the foregoing formulas T and Z have the meanings given hereinabove. 3-Amino-5-nitrobenozic acid or a derivative thereof is treated with an acid chloride, T—COC1, to yield a nitro amide (G') which is catalytically reduced to an amino amide (H). The latter is iodinated to give a 2,4,6-triiodo-3-amino-5-acylamidobenzoic acid or derivative thereof (J) and finally alkylated on the amide nitrogen to produce a compound of formula C where R° is (T—CO)N(lower-alkyl). The latter can be converted to compounds of formulas A and B by the methods previously described.

The compounds of the invention of formulas A and B where Y and/or Y' are alkylene groups interrupted by SO or SO₂ can alternatively be prepared by oxidation of the corresponding sulfide (—S—) compounds with a peracid. The oxidation takes place at room temperature in an inert organic solvent.

The key reaction in the foregoing methods for preparing the compounds of the invention is the formation of the cyclic imide from the substituted aniline. Prior art methods for the preparation of N-aryl cyclic imides comprise the formation of the N-aryl-anilic acid followed by cyclodehydration of the latter to form the N-aryl cyclic imide. The present invention provides a process for preparing N-aryl cyclic imides from substituted anilines in a single step.

A process aspect of the invention thus resides in a process for preparing compounds of the formula

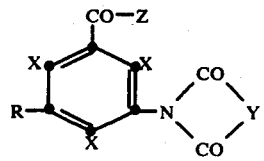

wherein R is

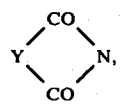

T-CO-NHCH$_2$, (T-CO)N(lower-alkyl), HOOC-Y-CO-N(lower-alkyl) or O$_2$N (Z and T having the meanings given above); Y is vinylene, a lower-alkylene group wherein 2 or 3 carbon atoms separate the carbonyl groups, or a 1,3-propylene group wherein the 2-carbon atom is replaced by O, S, SO or SO$_2$; and X is H or I, X being H when R is O$_2$N, which comprises heating a compound of the formula

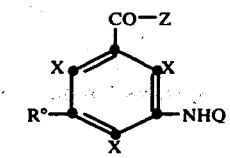

wherein R° is H$_2$N,

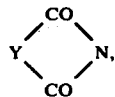

T-CO-NH, T-CO-NHCH$_2$, (T-CO)N(lower-alkyl), HOOC-Y-CO-N(lower-alkyl) or O$_2$N (Z and T having the meanings given above); Y is vinylene, a lower-alkylene group wherein 2 or 3 carbon atoms separate the carbonyl groups, or a 1,3-propylene group wherein the 2-carbon atom is replaced by O, S, SO or SO$_2$; Q is hydrogen or lower-alkanoyl; and X is H or I, X being H when R° is O$_2$N, with a compound of the formula

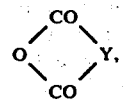

a strong acid catalyst preferably being used where Y is lower-alkylene. An equimolar quantity or an excess of the anhydride reactant is used, and the reactants are heated together at a temperature between about 50° C. and 150° C.

If desired, the cyclic imide of formula (K) can be hydrolyzed to the corresponding anilic acid of formula

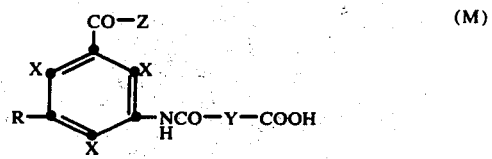

and the latter, if desired, where X is iodine, can be N-alkylated with R' halide, R' sulfate, R' alkylsulfonate or R' arylsulfonate, to give a compound of formula B wherein R' is lower-alkyl, hydroxy-lower-alkyl, lower-alkoxy-lower-alkyl or lower-alkoxy-lower-alkoxy-lower-alkyl.

The structures of the compounds of the invention were determined by the modes of synthesis, by elementary analysis and by neutral equivalent determinations. The course of the reactions was followed by thin-layer chromatography.

Those commpounds of the invention which are carboxylic acids, can be obtained in the form of salts derived from inorganic bases or organic amines. The compounds of formula B where R" is hydrogen and Z is OH, being dibasic acids, can form mono- or di-salts. Preferred salts are those which are pharmaceutically acceptable, for example, the sodium, magnesium, calcium and N-methylglucamine salts; although all salts are useful either as characterizing derivatives or as intermediates in the purification of the acids. The salt forms of the compounds of the invention are considered the full equivalents of the free acids claimed herein, and thus are part of the same inventive concept.

The compounds of the invention in the form of water-soluble, pharmaceutically acceptable salts are useful as intravenous X-ray contrast media either for visualization of the kidneys and urinary tract (urography) or of the gallbladder (cholecystography). The compounds of lower molecular weight, having from 11 to about 15 carbon atoms, are primarily urographic agents, whereas those of higher molecular weight and greater lipophilic character are primarily cholecystographic agents. The compounds have a low toxicity, intravenous LD$_{50}$ values ranging up to 20,000 mg./kg. in mice.

The actual quantitative determination of toxicity and radiopaque effectiveness for a particular compound is readily determined by standard test procedures by technicians trained in pharmacological test procedures, without the need for any extensive experimentation; Hoppe, J. Am. Pharmaceut. Assn. 48, 368–79 (1959); and Hoppe et al., Am. J. Roentgen. Rad. Therap. Nuc. Med. 69, 620–7 (1953).

The compounds of the invention were tested for their intravenous urographic or cholecystographic efficacy by standard procedure as follows. The test compound was injected intraveneously in the form of an aqueous solution of the sodium or N-methylglucamine salt to the test animals, usually cats or rabbits. Each animal was X-rayed at hourly intervals and the roentgenograms examined and evaluted. The density of the organ shadows was interpreted in accordance with a numerical scoring plan designated as the Cholecystographic Index (CI) or Urographic Index (UI), a measure of the efficiency of the test compound, viz.: 0 (none), 1 (POOR), 2 (fair), 3 (good), 4 (excellent). At a dose level of 100 mg./kg., the compounds of the invention having cholecystographic properties produced gallbladder shadows having a maximum Cholecystographic Index of 3.0–4.0.

The compounds of the invention are prepared for use by dissolving a pharmaceutically acceptable salt form in sterile aqueous medium suitable for intravenous injection.

The following examples will further illustrate the invention without the latter being limited thereby.

EXAMPLE 1

3-Glutarimido-5-(N-methylacetamido)-2,4,6-triiodobenzoic Acid [A; R is $CH_3CON(CH_3)$, Y is $CH_2CH_2CH_2$, Z is OH].

A mixture of 117.2 g. of 3-amino-5-(N-methylacetamido)-2,4,6-triiodobenzoic acid and 182 g. of glutaric anhydride was heated with stirring on a steam bath. Concentrated sulfuric acid (10 ml.) was added, and heating and stirring were continued for seven hours. The reaction mixture was added to 700 ml. of water, and the solid product was collected by filtration and recrystallized from acetic acid. The resulting 3-glutarimido-5-(N-methylacetamido)-2,4,6-triiodobenzoic acid was converted to its sodium salt form as follows: the free acid was slurried with 40 ml. of methanol and a 1N solution of sodium hydroxide in methanol was added with trituration until the solid had dissolved. The sodium salt was precipitated out with ether, and the resulting gum was triturated with ether and dissolved in methanol. The latter solution was decolorized with activated charcoal and the product reprecipitated with ether. The product was dissolved in water and the solution filtered and concentrated in vacuo. The residue was dried in vacuo to give the sodium salt of 3-glutarimido-5-(N-methylacetamido)-2,4,6-triiodobenzoic acid as a pale pink solid, m.p. 200°–204° C. (dec.).

When the glutaric anhydride in the foregoing preparation was replaced by glutaryl chloride in dioxane solution there was obtained a product in which 3-glutarimido-5-(N-methylacetamido)-2,4,6-triiodobenzoic acid could be identified by thin layer chromatography.

By replacing the 3-amino-5-(N-methylacetamido)-2,4,6-triiodobenzoic acid in the foregoing preparation by a molar equivalent amount of 3-amino-5-(N-butylacetamido)-2,4,6-triiodobenzoic acid, 3-amino-5-(N-methylpropionamido)-2,4,6-triiodobenzoic acid, 3-amino-5-(N-methylcaproylamino)-2,4,6-triiodobenzoic acid, 3-amino-5-(N,N-dimethylcarbamoyl)-2,4,6-triiodobenzoic acid, or 3-amino-5-(N-methyl-2-methoxyacetamido)-2,4,6-triiodobenzoic acid, there can be obtained, respectively, 3-glutarimido 5-(N-butylacetamido)-2,4,6-triiodobenzoic acid [A; R is $CH_3CON(C_4H_9)$, Y is $CH_2CH_2CH_2$, Z is OH], 3-glutarimido-5-(N-methylpropionamido)-2,4,6-triiodobenzoic acid [A; R is $CH_3CH_2CON(CH_3)$, Y is $CH_2CH_2CH_2$, Z is OH], 3-glutarimido-5-(N-methylcaproylamino)-2,4,6-triiodobenzoic acid [A; R is $CH_3(CH_2)_4CON(CH_3)$, Y is $CH_2CH_2CH_2$, Z is OH], 3-glutarimido-5-(N,N-dimethylcarbamoyl)-2,4,6-triiodobenzoic acid [A; R is $(CH_3)_2NCO$, Y is $CH_2CH_2CH_2$, Z is OH], or 3-glutarimido-5-(N-methyl-2-methoxyacetamido)-2,4,6-triiodobenzoic acid [A; R is $CH_3OCH_2CON(CH_3)$, Y is $CH_2CH_2CH_2$, Z is OH].

By replacing the glutaric anhydride in the foregoing preparation by a molar equivalent amount of 2,3-dimethylsuccinic anhydride, 2,3,4-trimethylglutaric anhydride, or 2-methylglutaric anhydride, there can be obtained, respectively, 3-(2,3-dimethylsuccinimido)-5-(N-methylacetamido)-2,4,6-triiodobenzoic acid [A; R is $CH_3CON(CH_3)$, Y is $CH(CH_3)CH(CH_3)$, Z is OH], 3-(2,3,4-trimethylglutarimido)-2,4,6-triiodobenzoic acid [A; R is $CH_3CON(CH_3)$, Y is $CH(CH_3)CH(CH_3)CH(CH_3)$, Z is OH], or 3-(2-methylglutarimido)-2,4,6-triiodobenzoic acid [A; R is $CH_3CON(CH_3)$, Y is $CH(CH_3)CH_2CH_2$, Z is OH].

EXAMPLE 2

3-Succinimido-5-(N-methylacetamido)-2,4,6-triiodobenzoic Acid

[A; R is $CH_3CON(CH_3)$, Y is $CH_2CH_2$, Z is OH]

was prepared from 87.9 g. of 3-amino-5-(N-methylacetamido)-2,4,6-triiodobenzoic acid, 120 g. of succinic anhydride and 6 ml. of sulfuric acid according to the procedure of Example 1, except that a reaction temperature of 130°–140° C. was used. The reaction was essentially complete after 30 minutes heating time. The compound was isolated in the form of its sodium salt, pale yellow solid, m.p. 220°–222° C. (dec.).

EXAMPLE 3

3-(3-Methylglutarimido)-5-(N-methylacetamido)-2,4,6-triiodobenzoic Acid

[A; R is $CH_3CON(CH_3)$, Y is $CH_2CH(CH_3)CH_2$, Z is OH]

was prepared from 3-amino-5-(N-methylacetamido-2,4,6-triiodobenzoic acid, 3-methylglutaric anhydride and sulfuric acid according to the procedure of Example 1. The product was isolated in the free acid form, m.p. 301°–302° C. (dec.) when recrystallized from acetic acid.

EXAMPLE 4

3,5-bis(Glutarimido)-2,4,6-triiodobenzoic Acid [A; R is $(CH_2)_3(CO)_2N$, Y is $CH_2CH_2CH_2$, Z is OH].

a. From 3,5-diamino-2,4,6-triiodobenzoic acid. A mixture of 265 g. of 3,5-diamino-2,4,6-triiodobenzoic acid, 400 g. of glutaric anhydride and 18 ml. of concentrated sulfuric acid was heated at 100° C. and stirred for seventeen hours. The product was isolated and recrystallized from dimethyl sulfoxide, adding water to induce precipitation, and was obtained as a light gray solid with one mole of dimethyl sulfoxide of crystallization, m.p. above 300° C. A sample of the acid was converted to its sodium salt form, m.p. 288°–291° C.(dec.) when recrystallized from water.

b. From 3-acetamido-5-amino-2,4,6-triiodobenzoic acid. A mixture of 11.4 g. of 3-acetamido-5- amino-2,4,6-triiodobenzoic acid, 23 g. of glutaric anhydride and 1 ml. of concentrated sulfuric acid was heated on a steam bath for two and one-half hours. The reaction mixture was stirred with water and the product (14.4 g.) collected by filtration. The product was recrystallized twice from acetone to give 3,5-bis(glutarimido)-2,4,6-triiodobenzoic acid. The same compound is obtained if the 3-acetamido-5-amino-2,4,6-triiodobenzoic acid is replaced by 3,5-diacetamido-2,4,6-triiodobenzoic acid.

The following compounds were prepared following the procedure of Example 1 from the appropriate 3-amino-5-R-2,4,6-triiodobenzoic acid and acid anhydride.

EXAMPLE 5

3-(3,3-Dimethylglutarimido)-5-(N-methylacetamido)-2,4,6-triiodobenzoic Acid [A; R is $CH_3CON(CH_3)$, Y is $CH_2C(CH_3)_2CH_2$, Z is OH], pale tan solid, m.p. 274°–278° C. (dec.) (from acetic acid); sodium salt form, pale yellow solid, m.p. 235°–245° C.(dec.).

EXAMPLE 6

3-Glutarimido-5-(N-ethylacetamido)-2,4,6-triiodobenzoic Acid

[A; R is $CH_3CON(C_2H_5)$, Y is $CH_2CH_2CH_2$, Z is OH], sodium salt form, m.p. above 220° C.

EXAMPLE 7

3-(Methylsuccinimido)-5-(N-methylacetamido)-2,4,6-triiodobenzoic Acid

[A; R is $CH_3CON(CH_3)$, Y is $CH(CH_3)CH_2CH_2$, Z is OH]

m.p. 285°–287° C. (from acetic acid); sodium salt form, m.p. above 245° C.(dec.).

EXAMPLE 8

3-(Diglycolimido)-5-(N-methylacetamido)-2,4,6-triiodobenzoic Acid [A; R is $CH_3CON(CH_3)$, Y is $CH_2OCH_2$, Z is OH], sodium salt form, m.p. 250°–255° C. No sulfuric acid was used in this preparation.

EXAMPLE 9

3-(3,5-Dioxothiomorpholino)-5-(N-methylacetamido)-2,4,6-triiodobenzoic Acid [A; R is $CH_3CON(CH_3)$, Y is $CH_2SCH_2$, Z is OH], sodium salt form, beige solid, m.p. 250°–260° C.(dec.). No sulfuric acid was used in this preparation.

3-(3,5-Dioxothiomorpholino)-5-(N-methylacetamido)-2,4,6-triiodobenzoic acid can be oxidized with m-chloroperbenzoic acid in dimethylformamide solution to give 3-(3,5,S,S-tetraoxothiomorpholino)-5-(N-methylacetamido)-2,4,6-triiodobenzoic acid [A; R is $CH_3CON(CH_3)$, Y is $CH_2SO_2CH_2$, Z is OH].

EXAMPLE 10

3'-Carboxy-5'-(N-methylacetamido)-2',4',6'-triiodoglutaranilic Acid [B; R is $CH_3CON(CH_3)$, R' and R" are H, Y' is $CH_2CH_2CH_2$, Z is OH].

A mixture of 58.6 g. of 3-amino-5-(N-methylacetamido)-2,4,6-triiodobenzoic acid, 74 g. of glutaric anhydride and 8 ml. of concentrated sulfuric acid was heated on a steam bath for five hours. The reaction mixture was poured into water and the solid product collected by filtration. The product, consisting of 3-glutarimido-5-(N-methylacetamido)-2,4,6-triiodobenzoic acid (Example 1) was dissolved in excess dilute aqueous sodium hydroxide, and the solution warmed for thirty minutes, then cooled and 3N hydrochloric acid added slowly until precipitation was complete. The solid product was collected and recrystallized first from acetone, then from acetic acid, and finally from water to give 3'-carboxy-5'-(N-methylacetamido)-2',4',6'-triiodoglutaranilic acid, colorless prisms, m.p. 188.8°–196.0° C.

Similarly, by warming in dilute aqueous sodium hydroxide, 3-glutarimido-5-(N-butylacetamido)-2,4,6-triiodobenzoic acid, 3-glutarimido-5-(N-methylpropionamido)-2,4,6-triiodobenzoic acid, 3-glutarimido-5-(N-methylcaproylamino)-2,4,6-triiodobenzoic acid, 3-glutarimido-5-(N,N-dimethylcarbamoyl)-2,4,6-triiodobenzoic acid, 3-(2,3-dimethylsuccinimido)-5-(N-methylacetamido)-2,4,6-triiodobenzoic acid, 3-(2,3,4-trimethylglutarimido)-5-(N-methylacetamido)-2,4,6-triiodobenzoic acid, 3-(2-methylglutarimido)-5-(N-methylacetamido)-2,4,6-triiodobenzoic acid, 3-(3-methylglutarimido)-5-(N-methylacetamido)-2,4,6-triiodobenzoic acid, or 3-glutarimido-5-(N-methyl-2-methoxyacetamido)-2,4,6-triiodobenzoic acid can be hydrolyzed, respectively, to 3'-carboxy-5'-(N-butylacetamido)-2',4',6'-triiodoglutaranilic acid [B; R is $CH_3CON(C_4H_9)$, R' and R" are H, Y' is $CH_2CH_2CH_2$, Z is OH], 3'-carboxy-5'-(N-methylpropionamido)-2',4',6'-triiodoglutaranilic acid [B; R is $CH_3CH_2CON(CH_3)$, R' and R" are H, Y' is $CH_2CH_2CH_2$, Z is OH], 3'-carboxy-5'-(N-methylcaproylamino)-2',4',6'-triiodoglutaranilic acid [B; R is $CH_3(CH_2)_4CON(CH_3)$, R' and R" are H, Y' is $CH_2CH_2CH_2$, Z is OH], 3'-carboxy-5'-(N,N-dimethylcarbamoyl)-2',4',6'-triiodoglutaranilic acid [B; R is $(CH_3)_2NCO$, R' and R" are H, Y' is $CH_2CH_2CH_2$, Z is OH], 3'-carboxy-5'-(N-methylacetamido)-2',4',6'-triiodo-2,3-dimethylsuccinanilic acid [B; R is $CH_3CON(CH_3)$, R' and R" are H, Y' is $CH(CH_3)CH(CH_3)$, Z is OH], 3'-carboxy-5'-(N-methylacetamido)-2',4',6'-triiodo-2,3,4-trimethylglutaranilic acid [B; R is $CH_3CON(CH_3)$, R' and R" are H, Y' is $CH(CH_3)CH(CH_3)—CH(CH_3)$, Z is OH], 3'carboxy-5'-(N-methylacetamido)-2',4',6'-triiodo-2(or 4)-methylglutaranilic acid [B; R is $CH_3CON(CH_3)$, R' and R" are H, Y' is $CH(CH_3)CH_2CH_2$ or $CH_2CH_2CH(CH_3)$, Z is OH], 3'-carboxy-5'-(N-methylacetamido)-2',4',6'-triiodo-3-methylglutaranilic acid [B; R is $CH_3CON(CH_3)$, R' and R" are H, Y' is $CH_2CH(CH_3)CH_2$, Z is OH], or 3'-carboxy-5'-(N-methyl-2-methoxyacetamido)-2',4',6'-triiodoglutaranilic acid [B; R is $CH_3OCH_2CON(CH_3)$, R' and R" are H, Y' is $CH_2CH_2CH_2$, Z is OH].

3'-Carboxy-5'-(N-methylacetamido)-2',4',6'-triiodoglutaranilic acid can also be prepared by heating 3-amino-5-(N-methylacetamido)-2,4,6-triiodobenzoic acid with 4-carbomethoxybutyryl chloride ($CH_3O-COCH_2CH_2CH_2COCl$) in dioxane solution followed by hydrolysis of the resulting methyl 3'-carboxy-5'-(N-methylacetamido)-2',4',6'-triiodoglutaranilate by heating it with potassium carbonate in methanol solution.

Similarly, 3-amino-5-(N-methylacetamido)-2,4,6-triiodobenzoic acid can be caused to react with $Cl-COCH_2CH_2CH_2CH_2COOCH_3$, $Cl-COCH_2CH_2OCH_2CH_2COOCH_3$ or $Cl-COCH_2SCH_2CH_2CH_2SCH_2COOCH_3$ to give, respectively, the following compounds: [B; R is $CH_3CON(CH_3)$, R' is H, R" is $CH_3$, Y' is $CH_2CH_2CH_2CH_2$, Z is OH]; [B; R is $CH_3CON(CH_3)$, R' is H, R" is $CH_3$, Y' is $CH_2CH_2OCH_2CH_2$, Z is OH]; or [B; R is $CH_3CON(CH_3)$, R' is H, R" is $CH_3$, Y' is $CH_2SCH_2CH_2CH_2SCH_2$, Z is OH]. These can be hydrolyzed to the corresponding dibasic acids where R" is hydrogen. In the same manner, 3,5-diamino-2,4,6-triiodobenzoic acid can be caused to react with $Cl—COCH_2CH_2CH_2CH_2COOCH_3$ to give [B; R is $CH_3OCOCH_2CH_2CH_2CH_2CONH$, R' is H, R" is $CH_3$, Y' is $CH_2CH_2CH_2CH_2$, Z is OH], which can be hydrolyzed to give [B; R is $HOCOCH_2CH_2CH_2CH_2CONH$, R' and R" are H, Y' is $CH_2CH_2CH_2CH_2$, Z is OH].

EXAMPLE 11

3'-Carboxy-5'-(N-methylacetamido)-2',4',6'-triiodosuccinanilic Acid [B; R is $CH_3CO$, R' and R'' are H, Y' is $CH_2CH_2$, Z is OH] was prepared from 34.3 g. of 3-amino-5-(N-methylacetamido)-2,4,6-triiodobenzoic acid, 82 g. of succinic anhydride and 5 ml. of concentrated sulfuric acid, followed by alkaline hydrolysis of the resulting 3-succinimido-5-(N-methylacetamido)-2,4,6-triiodobenzoic acid, according to the method described in Example 10. The product was recrystallized from dilute ethanol and from a methanol-acetonitrile mixture and further purified by converting it to the diammonium salt by means of ammonium hydroxide in methanol, and then acidifying an aqueous solution of the ammonium salt to regenerate the free acid. There was thus obtained 3'-carboxy-5'-(N-methylacetamido)-2',4',6'-triiodosuccinanilic acid, m.p. 275.0°–276.0° C.(dec.).

EXAMPLE 12

3-[2-(Carboxymethylsulfonyl)acetamido]-2,4,6-triiodo-5-(N-methylacetamido)benzoic Acid [B; R is $CH_3CON(CH_3)$, R' and R'' are H, Y' is $CH_2SO_2CH_2$, Z is OH].

A solution of 26.1 g. of 3-amino-5-(N-methylacetamido)-2,4,6-triiodobenzoic acid in 300 ml. of dioxane was distilled until about 60 ml. of dioxane was removed in order to eliminate possible traces of water. Sulfonyldiacetyl chloride ($ClCOCH_2SO_2CH_2COCl$) (5.85 g.) was then added, and the mixture was stirred and refluxed for about 5 days. The reaction mixture was concentrated in vacuo to remove the solvent, and the residue was dissolved in dilute sodium hydroxide to give a solution of the sodium salt of the product. The basic solution was made weakly acid, which did not cause precipitation of the acid form of the product, treated with activated charcoal at 60° C. and filtered. The filtrate was acidified with 3N hydrochloric acid and the precipitated product collected. The acid product was purified by dissolving it in ammonium hydroxide solution and reacidifying the resulting ammonium salt solution. The acid product was recrystallized from aqueous dimethylformamide to give 3-[2-(carboxymethylsulfonyl)acetamido]-2,4,6-triiodo-5-(N-methylacetamido)benzoic acid, m.p. above 300° C.

By replacing the sulfonyldiacetyl chloride in the foregoing preparation by sulfoxydiacetyl chloride ($ClCOCH_2$—SO—$CH_2COCl$) there can be obtained 3-[2-(carboxymethylsulfoxy)acetamido]-2,4,6-triiodo-5-(N-methylacetamido)benzoic acid [B; R is $CH_3CON(CH_3)$, R' and R'' are H, Y' is $CH_2SOCH_2$, Z is OH].

The following compounds were prepared either by mild alkaline hydrolysis of the corresponding cyclic imides, or directly from the appropriate 3-amino-5-R-2,4,6-triiodobenzoic acid without isolation of the intermediate cyclic imide as described above in Examples 10 and 11.

Example 13: 3'-Carboxy-2',4',6'-triiodo-3-methyl-5'-(N-methylacetamido)glutaranilic Acid [B; R is $CH_3CON(CH_3)$, R' and R'' are H, Y' is $CH_2CH(CH_3)CH_2$, Z is OH], colorless crystals, m.p. 256°–259° C.(dec.).

Example 14: 3,5-bis(4-Carboxybutyramido)-2,4,6-triiodobenzoic Acid [B; R is $HOOC(CH_2)_3CONH$, R' and R'' are H, Y' is $CH_2CH_2CH_2$, Z is OH], colorless solid, m.p. 251°–253° C. (from acetic acid).

Example 15: 3'-Carboxy-2',4',6'-triiodo-3,3-dimethyl-5'-(N-methylacetamido)glutaranilic Acid [B; R is $CH_3CON(CH_3)$, R' and R'' are H, Y' is $CH_2C(CH_3)_2CH_2$, Z is OH], colorless crystals, m.p. 258°–262° C. (dec.).

Example 16: 3'-Carboxy-5'-(N-ethylacetamido)-2',4',6'-triiodoglutaranilic Acid [B; R is $CH_3CON(C_2H_5)$, R' and R'' are H, Y' is $CH_2CH_2CH_2$, Z is OH], colorless solid, m.p. 250° C. (dec.).

Example 17: 3'-Carboxy-2',4',6'-triiodo-3-methyl-5'-(N-methylacetamido)succinanilic Acid [B; R is $CH_3CON(CH_3)$, R' and R'' are H, Y' is $CH(CH_3)CH_2$, Z is OH], light orange solid, m.p. 262°–264° C. (dec.).

Example 18: 3'-Carboxy-2',4',6'-triiodo-5'-(N-methylacetamido) diglycolanilic Acid [B; R is $CH_3CON(CH_3)$, R' and R'' are H, Y' is $CH_2OCH_2$, Z is OH], disodium salt form, light tan solid, m.p. 245°–260° C. (dec.).

Example 19: 3-[2-(Carboxymethylthio)acetamido]-2,4,6-triiodo-5-(N-methylacetamido)benzoic Acid [B; R is $CH_3CON(CH_3)$, R' and R'' are H, Y' is $CH_2SCH_2$, Z is OH], beige solid, m.p. 165–170° C.

EXAMPLE 20 a. 3-Succinimido-5-nitrobenzoic Acid [D; Y is $CH_2CH_2$, Z is OH] was prepared by heating 3-amino-5-nitrobenzoic acid with succinic anhydride in the presence of sulfuric acid. It had the m.p. 285°–290° C. when recrystallized from aqueous dimethylformamide. b. 3'-Carboxy-5'-nitrosuccinanilic Acid [F; Y is $CH_2CH_2$, Z is OH] was prepared by treating 3-succinimido-5-nitrobenzoic acid with warm dilute aqueous sodium hydroxide, and had the m.p. 220°–221° C.

c. 3'-Carboxy-5'-aminosuccinanilic Acid [G; Y is $CH_2CH_2$, Z is OH].

3'-Carboxy-5'-nitrosuccinanilic acid (83.5 g.) and 50 ml. of concentrated ammonium hydroxide in 100 ml. of water were added to a heated solution of 540 g. of ferrous sulfate heptahydrate in 900 ml. of water. Concentrated ammonium hydroxide (100 ml.) was then added during fifteen minutes in 50 ml. portions. After thirty minutes of heating on a steam bath, the reaction mixture was filtered and made acid to pH 3.5. The product was collected and dried in vacuo over phosphorus pentoxide to give 57.5 g. of 3'-carboxy-5'-aminosuccinanilic acid, m.p. 194° C. (dec.).

d. 3'-Carboxy-5'-amino-2',4',6'-triiodosuccinanilic Acid [B; R is $NH_2$, R' and R'' are H, Y' is $CH_2CH_2$, Z is OH].

Potassium iododichloride (335 ml. 2.23N in water), was added over a period of forty minutes to a stirred suspension of 57.3 g. of 3'-carboxy-5'-aminosuccinanilic acid in 435 ml. of water. The solid product was collected by filtration and recrystallized from water and from aqueous dimethylformamide. The product was purified by converting it to the diammonium salt and then to the disodium salt, m.p. 222°–225° C. (dec.). The latter was acidified to produce the free acid form of 3'-carboxy-5'-amino-2',4',6'-triiodosuccinanilic acid, cream colored solid, m.p. 156.2°–172.2° C. (dec.). 3'-Carboxy-5'-amino-2',4',6'-triiodosuccinanilic acid can be acylated with acetic anhydride, using a few drops of perchloric acid as a catalyst to obtain 3'-carboxy-5'-acetamido-2',4',6'-triiodosuccinanilic acid [B; R is $CH_3CONH$, R' and R'' are H, Y' is $CH_2CH_2$, Z is OH].

EXAMPLE 21 a. 3-Glutarimido-5-nitrobenzoic Acid [D; Y is $CH_2CH_2CH_2$, Z is OH] was prepared by heating a mixture of 18.2 g. of 3-amino-5-nitrobenzoic acid, 45.6 g. of glutaric anhydride and 0.5 ml. of concentrated sulfuric acid on a steam bath for two hours. The product was isolated and recrystallized from aqueous dimethylformamide to give 3-glutarimido-5-nitrobenzoic acid, pale yellow prisms, m.p. above 300° C.

3'-Carboxy-5'-nitroglutaranilic Acid [F; Y is $CH_2CH_2CH_2$, Z is OH] was prepared by warming gently a solution of 5.0 g. of 3-glutarimido-5-nitrobenzoic acid in excess 10% aqueous sodium hydroxide. The solution was acidified with 3N hydrochloric acid and the product collected and recrystallized from ethyl acetate to give 3'-carboxy-5'-nitroglutaranilic acid, pale yellow prisms, m.p. 182°–184° C.

c. 3'-Carboxy-5'-aminoglutaranilic Acid [G; Y is $CH_2CH_2CH_2$, Z is OH].

3-Glutarimido-5-nitrobenzoic acid (55.6 g.) was dissolved in 150 ml. of 10% aqueous sodium hydroxide, the pH adjusted to 8 with 3N hydrochloric acid, 1.0 g. of 10% palladium-on-carbon catalyst added, and the mixture hydrogenated in a Parr apparatus. Reduction was complete in five hours. The reaction mixture was filtered and the filtrate containing 3'-carboxy-5'-aminoglutaranilic acid iodinated as described below.

d. 3'-Carboxy-5'-amino-2',4',6'-triiodoglutaranilic Acid [B; R is $H_2N$, R' and R'' are H, Y' is $CH_2CH_2CH_2$, Z is OH].

The filtrate containing 3'-carboxy-5'-aminoglutaranilic acid was diluted with water to 800 ml. and 100 ml. of 6N hydrochloric acid added, followed by 500 ml. of 1.28N sodium iododichloride. The reaction mixture was stirred for about sixteen hours, sodium bisulfite solution added to destroy excess iodine and the solid product collected. The latter was converted to its diammonium salt with ammonium hydroxide in isopropyl alcohol, the salt collected, dissolved in water, and the solution acidified with hydrochloric acid. The free acid was collected and dried at 60° C. to give 3'-carboxy-5'-amino-2',4',6'-triiodoglutaranilic acid, m.p. 219–221° C. (dec.).

EXAMPLE 22 a. 3-Glutarimido-5-aminobenzoic Acid [E; Y is $CH_2CH_2CH_2$, Z is OH] can be prepared by reduction of 3-glutarimido-5-nitrobenzoic acid (Example 21a). The reduction can be carried out catalytically (platinum or nickel catalyst) under neutral or acidic conditions.

b. 3-Glutarimido-5-amino-2,4,6-triiodobenzoic Acid [A; R is $H_2N$, Y is $CH_2CH_2CH_2$, Z is OH] can be prepared by iodination of 3-glutarimido-5-aminobenzoic acid with potassium iododichloride according to the procedure described in Example 20, part (d).

c. 3-Glutarimido-5-acetamido-2,4,6-triiodobenzoic Acid [A; R is $CH_3CONH$, Y is $CH_2CH_2CH_2$, Z is OH] can be prepared by acetylation of 3-glutarimido-5-amino-2,4,6-triiodobenzoic acid with acetic anhydride, using a few drops of perchloric acid as a catalyst.

EXAMPLE 23 a. 3'-Carboxy-5'-nitrodiglycolanilic Acid [F; Y is $CH_2OCH_2$, Z is OH], pale yellow prisms, m.p. 216°–219° C. (from water), was prepared from 3-amino-5-nitrobenzoic acid and diglycolic anhydride.

b. 3'-Carboxy-5'-aminodiglycolanilic Acid [G; Y is $CH_2OCH_2$, Z is OH] was prepared by hydrogenation of 3-carboxy-5-nitrodiglycolanilic acid with palladium-on-carbon catalyst. It was iodinated in the following step without purification.

c. 3'-Amino-5'-carboxy-2',4',6'-triiododiglycolanilic Acid [B; R is $H_2N$, R' and R'' are H, Y' is $CH_2OCH_2$, Z is OH], pale cream-gray prisms, m.p. 220°–223° C. (dec.) (from acetic acid), was prepared by iodination of 3-carboxy-5-aminodiglycolanilic acid with potassium iodidichloride.

EXAMPLE 24

3'-Carboxy-5'-amino-2',4',6'-triiodo-N-methylglutaranilic Acid [B; R is $H_2N$, R' is $CH_3$, R'' is H, Y' is $CH_2CH_2CH_2$, Z is OH].

To a solution of 26.0 g. of 3'-carboxy-5'-amino-2',4',6'-triiodoglutaranilic acid (Example 21, part d) in 100 ml. of 10% aqueous sodium hydroxide cooled in an ice bath was added 8 ml. of dimethyl sulfate in acetone. After three hours of stirring an additional 15 ml. of 10% sodium hydroxide and 2 ml. of dimethyl sulfate were added and the mixture stirred three hours longer. The reaction mixture was acidified, and the product collected and recrystallized from acetic acid to give 3'-carboxy-5'-amino-2',4',6'-triiodo-N-methylglutaranilic acid, pale gray crystals, m.p. 218°–220° C. (dec.).

EXAMPLE 25

3'-Carboxy-5'-glutarimido-2',4',6'-triiodo-N-methylglutaranilic Acid [A; R is $HOOC(CH_2)_3CON(CH_3)$, Y is $CH_2CH_2CH_2$, Z is OH] was prepared from 3'-carboxy-5'-amino-2',4',6'-triiodo-N-methylglutaranilic acid (Example 24) and glutaric anhydride according to the procedure of Example 1. The free acid was obtained as a colorless solid, m.p. 160°–161° C. when recrystallized from acetic acid, and the disodium salt form as a beige solid, m.p. 252°–255° C.

EXAMPLE 26

3'-Carboxy-5'-(N-methylacetamido)-2',4',6'-triiodo-N-methylglutaranilic Acid [B; R is $CH_3CON(CH_3)$, R' is $CH_3$, R'' is H, Y' is $CH_2CH_2CH_2$, Z is OH] was prepared from 49.0 g. of 3'-carboxy-5'-(N-methylacetamido)-2',4',6'-triiodoglutaranilic acid (Example 10) and 15 ml. of dimethyl sulfate in 175 ml. of 10% sodium hydroxide according to the procedure of Example 24. The product was recrystallized from acetic acid, using ethyl acetate to bring the compound out of solution. There was thus obtained 3'-carboxy-5'-(N-methylacetamido)-2',4',6'-triiodo-N-methylglutaranilic acid, colorless prisms, m.p. 284°–287° C. (dec.).

EXAMPLE 27

3'-Carboxy-5'-(N-methylacetamido)-2',4',6'-triiodo-N-ethylglutaranilic Acid [B; R is $CH_3CON(CH_3)$, R' is $C_2H_5$, R'' is H, Y' is $CH_2CH_2CH_2$, Z is OH] was prepared from 56.3 g. of 3'-carboxy-5'-(N-methylacetamido)-2',4',6'-triiodoglutaranilic acid (Example 10) and 40 ml. of diethyl sulfate in 10% sodium hydroxide solution according to the procedure of Example 24. The product was recrystallized from acetic acid and from an acetic acid-ethyl acetate mixture to give 3'-carboxy-5'-(N-methylacetamido)-2',4',6'-triiodo-N-ethylglutaranilic acid, m.p. 259°–261° C.(dec.).

3'-Carboxy-5'-(N-methylacetamido)-2',4',6'-triiodoglutaranilic acid can similarly be alkylated with n-butyl iodide, 2-hydroxyethyl bromide, 2-ethoxyethyl bromide or 2-(2-ethoxyethoxy)ethyl p-toluenesulfonate to give 3'-carboxy-5'-(N-methylacetamido)-2',4',6'-triiodo-N-butylglutaranilic acid [B; R is $CH_3CON(CH_3)$, R' is $C_4H_9$, R" is H, Y' is $CH_2CH_2CH_2$, Z is OH], 3'-carboxy-5'-(N-methylacetamido)-2',4',6'-triiodo-N-(2-hydroxyethyl)glutaranilic acid [B; R is $CH_3CON(CH_3)$, R' is $HOCH_2CH_2$, R" is H, Y' is $CH_2CH_2CH_2$, Z is OH]; 3'-carboxy-5'-(N-methylacetamido)-2',4',6'-triiodo-N-(2-ethoxyethyl)-glutaranilic acid [B; R is $CH_3CON(CH_3)$, R' is $C_2H_5OCH_2CH_2$, R" is H, Y' is $CH_2CH_2CH_2$, Z is OH]or 3'-carboxy-5'-(N-methylacetamido)-2',4',6'-triiodo-N-[2-(2-ethoxyethoxy)ethyl]glutaranilic acid [B; R is $CH_3CON(CH_3)$, R' is $C_2H_5OCH_2CH_2OCH_2CH_2$, R" is H, Y' is $CH_2CH_2CH_2$, Z is OH].

According to the procedure of Example 24, the following compounds were prepared:

Example 28: 3'-Carboxy-2',4',6'-triiodo-3,N-dimethyl-5'-(N-methylacetamido)glutaranilic Acid [B; R is $CH_3CON(CH_3)$, R' is $CH_3$, R" is H, Y' is $CH_2CH(CH_3)CH_2$, Z is OH], colorless solid, m.p. 221°–222° C. (from acetic acid), prepared by methylation of 3'-carboxy-2',4',6'-triiodo-3-methyl-5'-(N-methylacetamido) glutaranilic acid (Example 13). Example 29: 3,5-bis(4-Carboxy-M-methylbutyramido)-2,4,6-triiodobenzoic Acid [B; R is $HOOC(CH_2)_3CON(CH_3)$, R' is $CH_3$, R" is H, Y' is $CH_2CH_2CH_2$, Z is OH], colorless prisms, m.p. 234°–236° C. (from acetic acid), prepared by methylation of 3,5-bis(4-carboxybutyramido)-2,4,6-triiodobenzoic acid (Example 14).

Example 30: 3'-Carboxy-2', 4', 6'-triiodo-N-methyl-5'-(N-methylacetamido)diglycolanilic Acid [B; R is $CH_3CON(CH_3)$, R' is $CH_3$, R" is H, Y' is $CH_2OCH_2$, Z is OH], colorless solid, m.p. 267°–272° C., prepared by methylation of 3'-carboxy-2',4',6'-triiodo-5'-(N-methylacetamido)diglycolanilic acid (Example 18).

Example 31: 3-[2-(Carboxymethylthio)-N-methylacetamido]-2,4,6-triiodo-5-(N-methylacetamido)benzoic Acid [B; R is $CH_3CON(CH_3)$, R' is $CH_3$, R" is H, Y' is $CH_2SCH_2$, Z is OH], light tan solid, m.p. 260°–265° C. (dec.), prepared by methylation of 3-[2-(carboxymethylthio)acetamido]-2,4,6-triiodo-5-(N-methylacetamido)-benzoic acid (Example 19).

Example 32: 3'-Carboxy-2',4',6'-triiodo-5'-(N-methylacetamido)-3,3,N-trimethylglutaranilic Acid [B; R is $CH_3CON(CH_3)$, R' is $CH_3$, R" is H, Y' is $CH_2C(CH_3)_2CH_2$, Z is OH], m.p. 183°–184.5° C., prepared by methylation of 3'-carboxy-2',4',6'-triiodo-3,3-dimethyl-5'-(N-methylacetamido)glutaranilic acid (Example 15).

EXAMPLE 33

Methyl 3'-carboxy-2',4',6'-triiodo-5'-(N-methylacetamido)adipanilate [B; R is $CH_3CON(CH_3)$, R' is H, R" is $CH_3$, Y' is $(CH_2)_4$, Z is OH].

A mixture of 98.4 g. of adipic acid monomethyl ester and 500 ml. of thionyl chloride was refluxed for one hour. The excess thionyl chloride was then removed in vacuo, and the last traces of thionyl chloride were removed by adding benzene and concentrating the solution. To the residue was added 260 g. of 3-amino-5-(N-methylacetamido)-2,4,6-triiodobenzoic acid in 3500 ml. of dioxane. The mixture was refluxed for about 36 hours and allowed to stand for two days at room temperature. The solid product was collected and recrystallized from acetic acid to give methyl 3'-carboxy-2',4',6'-triiodo-5'-(N-methylacetamido)adipanilate as a colorless solid, m.p. 229°–232° C.

Methyl 3'-carboxy-2',4',6'-triiodo-5'-(N-methylacetamido)adipanilate was obtained in the form of its sodium salt by treating the free acid with methanolic sodium hydroxide. The sodium salt had the m.p. 264°–267° C. (dec.).

EXAMPLE 34

3'-Carboxy-2',4',6'-triiodo-5'-(N-methylacetamido)adipanilic Acid [B; R is $CH_3CON(CH_3)$, R' and R" are H, Y' is $(CH_2)_4$, Z is OH].

To a mixture of 143.8 g. of methyl 3'-carboxy-2',4',6'-triiodo-5'-(N-methylacetamido)adipanilate (Example 33) and 150 ml. of water was added dropwise 145 ml. of 10% sodium hydroxide solution. The reaction mixture was heated on a steam bath for two hours and then cooled and acidified with 3N hydrochloric acid solution. The solid product was collected and recrystallized from acetic acid to give 3'-carboxy-2',4',6'-triiodo-5'-(N-methylacetamido)adipanilic acid in the form of a colorless solid, m.p. 267°–271° C. (dec.).

EXAMPLE 35

3'-Carboxy-2',4',6'-triiodo-N-methyl-5'-(N-methylacetamido)adipanilic Acid [B; R is $CH_3CON(CH_3)$, R' is $CH_3$, R" is H, Y' is $(CH_2)_4$, Z is OH] was prepared by methylation of 3'-carboxy-2',4',6'-triiodo-5'-(N-methylacetamido)adipanilic acid (Example 34) with dimethyl sulfate according to the procedure described in Example 24. The product was purified through the sodium salt and then recrystallized from acetic acid to give 3'-carboxy-2',4',6'-triiodo-N-methyl-5'-(N-methylacetamido)adipanilic acid in the form of a colorless solid, m.p. 194°–204° C.

EXAMPLE 36

2,4,6-Triiodo-3 -{3-[2-(methoxycarbonyl)ethylthio]propionamido}-5-(N-methylacetamido)benzoic Acid [B; R is $CH_3CON(CH_3)$, R' is H, R" is $CH_3$, Y' is $CH_2CH_2SCH_2CH_2$, Z is OH] was prepared from 225 g. of 3-amino-5-(N-methylacetamido)-2,4,6-triiodobenzoic acid and 80.52 g. of $ClCOCH_2CH_2SCH_2CH_2COOCH_3$ in 1170 ml. of dioxane according to the procedure described above in Example 33. The product was recrystallized from a methanol-acetonitrile mixture and was obtained as a colorless solid, m.p. 230°–240° C. (dec.).

The sodium salt form of 2,4,6-triiodo-3-{3-[2-(methoxycarbonyl)ethylthio]propionamido}-5-(N-methylacetamido)benzoic acid, prepared from the free acid and methanolic sodium hydroxide, was obtained as a colorless solid, m.p. 220°–270° C.

EXAMPLE 37

3-[3-(2-Carboxyethylthio)propionamido]-2,4,6-triiodo-5-(N-methylacetamido)benzoic Acid [B; R is $CH_3CON(CH_3)$, R' and R" are H, Y' is $CH_2CH_2SCH_2CH_2$, Z is OH] was prepared by hydrolysis of 2,4,6-triiodo-3-{3-[2-(methoxycarbonyl)ethylthio]propionamido}-5-(N-methylacetamido)benzoic acid (Example 36) with sodium hydroxide according to the procedure described above in Example 34, and was obtained as a yellow solid, m.p. 228°-243° C. (dec.)

EXAMPLE 38

Methyl 3'-carboxy-2',4',6'-triiodo-5'-(N-methylacetamido)azelanilate [B; R is $CH_3CON(CH_3)$, R' is H, R" is $CH_3$, Y' is $(CH_2)_7$, Z is OH].

A mixture of 100 g. of azelaic acid monomethyl ester and 500 ml. of thionyl chloride was refluxed for one hour. The excess thionyl chloride was removed by distillation and the last traces removed by adding benzene and evaporating the solvent. A solution of 260 g. of 3-amino-5-acetamido-2,4,6-triiodobenzoic acid in 3500 ml. of dioxane was then added to the resulting acid chloride of azelaic acid monomethyl ester, and the mixture was refluxed for six hours. The dioxane was then removed by distillation and the residual product recrystallized from acetic acid to give methyl 3'-carboxy-2',4',6'-triiodo-5'-(N-methylacetamido)azelanilate, as colorless needles, m.p. 198°-203° C.

By replacing the azelaic acid monomethyl ester by a molar equivalent amount of oxalic acid monomethyl ester or malonic acid monomethyl ester, there can be obtained, respectively, methyl 3'-carboxy-2',4',6'-triiodo-5'-(N-methylacetamido)oxalanilate [B; R is $CH_3CON(CH_3)$, R' is H, R" is $CH_3$, Y' is single bond, Z is OH], or methyl 3'-carboxy-2',4',6'-triiodo-5'-(N-methylacetamido)malonanilate [B; R is $CH_3CON(CH_3)$, R' is H, R" is $CH_3$, Y' is $CH_2$, Z is OH].

The sodium salt form of methyl 3'-carboxy-2',4',6'-triiodo-5'-(N-methylacetamido)azelanilate was obtained in the form of a colorless solid, m.p. 197°-204° C. (dec.).

EXAMPLE 39

3'-Carboxy-2',4',6'-triiodo-5'-(N-methylacetamido)azelanilic Acid [B; R is $CH_3CON(CH_3)$, R' and R" are H, Y' is $(CH_2)_7$, Z is OH].

A mixture of 136.5 g. of methyl 3'-carboxy-2',4',6'-triiodo-5'-(N-methylacetamido)azelanilate and 180 ml. of water was treated with 10% aqueous sodium hydroxide (about 140 ml.), added dropwise until solution was complete. The mixture was heated on a steam bath for ten minutes, 18 ml. more of 10% sodium hydroxide was added, and the mixture heated one hour longer. The reaction mixture was cooled, acidified with 3% hydrochloric acid, and the solid product collected, washed with water, dried and recrystallized from acetic acid to give 3'-carboxy-2',4',6'-triiodo-5'-(N-methylacetamido)azelanilic acid as a colorless solid, m.p. 205°-208° C.

By replacing the methyl 3'-carboxy-2',4',6'-triiodo-5'-(N-methylacetamido)azelanilate by a molar equivalent amount of methyl 3'-carboxy-2',4',6'-triiodo-5'-(N-methylacetamido)oxalanilate or methyl 3'-carboxy-2',4',6'-triiodo-5'-(N-methylacetamido)malonanilate there can be obtained, respectively, 3'-carboxy-2',4',6'-triiodo-5'-(N-methylacetamido)oxalanilic acid [B; R is $CH_3CON(CH_3)$, R' and R" are H, Y' is single bond, Z is OH] or 3'-carboxy-2',4',6'-triiodo-5'-(N-methylacetamido)malonanilic acid [B; R is $CH_3CON(CH_3)$, R' and R" are H, Y' is $CH_2$, Z is OH].

EXAMPLE 40

3'-Carboxy-2',4',6'-triiodo-N-methyl-5'-(N-methylacetamido)azelanilic Acid [B; R is $CH_3CON(CH_3)$, R' is $CH_3$, R" is H, Y' is $(CH_2)_7$, Z is OH] was prepared by methylation of 3'-carboxy-2',4',-6'-triiodo-5'-(N-methylacetamido)azelanilic acid (Example 39) with dimethyl sulfate according to the procedure of Example 24, and was obtained as a colorless solid, m.p. 210°-215° C., when recrystallized from ethyl acetate.

EXAMPLE 41

N-[2,4,6-Triiodo-3-(acetylaminomethyl)-5-carboxyphenyl]glutarimide [A; R is $CH_3CONHCH_2$, Y is $CH_2CH_2CH_2$, Z is OH] was prepared by interacting 3-acetamido-5-acetamidomethyl-2,4,6-triiodobenzoic acid with glutaric anhydride according to the method of Example 1 and was obtained in the form of a colorless solid, m.p. 256°-268° C., when recrystallized from acetic acid.

The sodium salt form of N-[2,4,6-triiodo-3-(acetylaminomethyl)-5-carboxyphenyl]glutarimide was obtained as a colorless solid, m.p 252°-256° C.

EXAMPLE 42

N-[2,4,6-Triiodo-3-(acetylaminomethyl)-5-carboxyphenyl]glutaramic Acid [B; R is $CH_3CONHCH_2$, R' and R" are H, Y' is $CH_2CH_2CH_2$, Z is OH] was prepared by hydrolysis of N-[2,4,6-triiodo-3-(acetylaminomethyl)-5-carboxyphenyl]glutarimide (Example 41) with dilute sodium hydroxide, and was obtained in the form of a colorless solid, m.p. 234°-239° C. when recrystallized from acetic acid.

EXAMPLE 43

N-[2,4,6-Triiodo-3-(acetylaminomethyl)-5-carboxyphenyl]-N-methylglutaramic Acid [B; R is $CH_3CONHCH_2$, R' is $CH_3$, R" is H, Y' is $CH_2CH_2CH_2$, Z is OH] was prepared by methylation of N-[2,4,6-triiodo-3-(acetylaminomethyl)-5-carboxyphenyl]glutaramic acid (Example 42) with dimethyl sulfate according to the procedure described in Example 24, and was obtained in the form of a colorless solid, m.p. 276°-280° C. when recrystallized from aqueous dimethylformamide.

EXAMPLE 44

2,4,6-Triiodo-3-maleimido-5-(N-methylacetamido)-benzoic Acid [A; R is $CH_3CON(CH_3)$, Y is CH=CH, Z is OH] was prepared from 60 g. of 3-amino-5-(N-methylacetamido)-2,4,6-triiodobenzoic acid and 234.4 g. of maleic anhydride according to the procedure described above in Example 1, and was obtained as a colorless solid, m.p. 312° C. (dec.) when recrystallized from methanol.

2,4,6-Triiodo-3-maleimido-5-(N-methylacetamido)-benzoic acid can be hydrolyzed with dilute sodium hydroxide to give 3'-carboxy-5'-(N-methylacetamido)-2',4',6',-triiodomaleanilic acid [B; R is $CH_3CON(CH_3)$, R' and R" are H, Y' is CH=CH, Z is OH].

EXAMPLE 45 a. 3-Amino-2,4,6-triiodo-5-(N-methylacetamido)-N,N-dimethylbenzamide [C; R° is $CH_3CON(CH_3)$, Q is H, Z is $N(CH_3)_2$].

The acid chloride (16.23 g.) prepared from 3-amino-5-(N-methylacetamido)-2,4,6-triiodobenzoic acid and thionyl chloride was interacted with 60 ml. of dimethylamine (40% in water), 20 ml. of 35% aqueous sodium hydroxide and 30 ml. of water. The product was isolated and recrystallized from isopropyl alcohol to give 3-amino-2,4,6-triiodo-5-(N-methylacetamido)N,N-dimethylbenzamide as a pale yellow solid, m.p. 235°–240° C.

b. 3-Glutarimido-2,4,6-triiodo-5-(N-methylacetamido)-N,N-dimethylbenzamide [A; R is $CH_3CON(CH_3)$, Y is $CH_2CH_2CH_2$, Z is $N(CH_3)_2$] was prepared from 3-amino-2,4,6-triiodo-5-(N-methylacetamido)-N,N-dimethylbenzamide and glutaric anhydride according to the procedure described above in Example 1, and was obtained as a colorless solid, m.p. 299°–303° C. when recrystallized from aqueous dimethylformamide.

EXAMPLE 46

3'-(Dimethylcarbamoyl)-2',4',6'-triiodo-5'-(N-methylacetamido)glutaranilic Acid [B; R is $CH_3CON(CH_3)$, R' and R" are H, Y' is $CH_2CH_2CH_2$, Z is $N(CH_3)_2$] was prepared by hydrolysis of 3-glutarimido-2,4,6-triiodo-5-(N-methylacetamido)-N,N-dimethylbenzamide (Example 45, part b) with dilute sodium hydroxide according to the procedure of Example 10, and was obtained as a colorless solid, m.p. 265°–268° C. when recrystallized from acetic acid.

EXAMPLE 47

3'-(Dimethylcarbamoyl)-2',4',6'-triiodo-5'-(N-methylacetamido)-N-methylglutaranilic Acid [B; R is $CH_3CON(CH_3)$, R' is $CH_3$, R" is H, Y' is $CH_2CH_2CH_2$, Z is $N(CH_3)_2$] was prepared by methylation of 3'-(dimethylcarbamoyl)-2',4',6'-triiodo-5'-(N-methylacetamido)glutaranilic acid (Example 46) with dimethyl sulfate according to the procedure of Example 24, and was obtained as a colorless solid, m.p. 209°–214° C.

EXAMPLE 48

2,4,6-Triiodo-3-(N-methylacetamido)-5-(3-methylglutarimido)-N,N-dimethylbenzamide [A; R is $CH_3CON(CH_3)$, Y is $CH_2CH(CH_3)CH_2$, Z is $N(CH_3)_2$] was prepared from 3-amino-5-(N-methylacetamido)-2,4,6-triiodobenzoic acid and 3-methylglutaric anhydride according to the procedure described in Example 1, and was obtained as a colorless solid, m.p. 275°–282° C. when recrystallized from acetic acid.

EXAMPLE 49

3'-(Dimethylcarbamoyl)-2',4',6'-triiodo-5'-(N-methylacetamido)-3-methylglutaranilic Acid [B; R is $CH_3CON(CH_3)$, R' and R" are H, Y' is $CH_2CH(CH_3)CH_2$, Z is $N(CH_3)_2$] was prepared by hydrolysis of 2,4,6-triiodo-3-(N-methylacetamido)-5-(3-methylglutarimido)-N,N-dimethylbenzamide (Example 48) with dilute sodium hydroxide according to the procedure described in Example 10, and was obtained as a colorless solid, m.p. 244°–254° C. when recrystallized from isopropyl alcohol.

EXAMPLE 50 a. 4-[3-Amino-2,4,6-triiodo-5-(N-methylacetamido)benzoyl]morpholine [C; R° is $CH_3CON(CH_3)$, Q is H, Z is morpholino] was prepared from the acid chloride of 3-amino-5-(N-methylacetamido)-2,4,6-triiodobenzoic acid and morpholine according to the procedure described in Example 45, part (a). The product obtained was used directly in the procedure described in part (b) below.

By replacing the morpholine by piperidine or pyrrolidine there can be obtained, respectively, 1-[3-amino-2,4,6-triiodo-5-(N-methylacetamido)benzoyl]piperidine [C; R° is $CH_3CON(CH_3)$, Q is H, Z is piperidino] or 1-[3-amino-2,4,6-triiodo-5-(N-methylacetamido)-benzoyl]pyrrolidine [C; R° is $CH_3CON(CH_3)$, Q is H, Z is pyrrolidino].

b. 4-[3-Glutarimido-2,4,6-triiodo-5-(N-methylacetamido)benzoyl]morpholine [A; R is $CH_3CON(CH_3)$, Y is $CH_2CH_2CH_2$, Z is morpholino] was prepared from 4-[3-amino-2,4,6-triiodo-5-(N-methylacetamido)benzoyl]morpholine and glutaric anhydride according to the procedure of Example 1, and was obtained as a colorless solid, m.p. 293°–299° C. when recrystallized from acetic acid.

By replacing the 4-[3-amino-2,4,6-triiodo-5-(N-methylacetamido)benzoyl]morpholine by 1-[3-amino-2,4,6-triiodo-5-(N-methylacetamido)benzoyl]piperidine or 1-[3-amino-2,4,6-triiodo-5-(N-methylacetamido)benzoyl]pyrrolidine, there can be obtained, respectively, 1-[3-glutarimido-2,4,6-triiodo-5-(N-methylacetamido)benzoyl]piperidine [A; R is $CH_3CON(CH_3)$, Y is $CH_2CH_2CH_2$, Z is piperidino] or 1-[3-glutarimido-2,4,6-triiodo-5-(N-methylacetamido)benzoyl]pyrrolidine [A; R is $CH_3CON(CH_3)$, Y is $CH_2CH_2CH_2$, Z is pyrrolidino].

EXAMPLE 51

2',4',6'-Triiodo-3'-(N-methylacetamido)-5'-(morpholinocarbonyl)glutaranilic Acid [B; R is $CH_3CON(CH_3)$, R' and R" are H, Y' is $CH_2CH_2CH_2$, Z is morpholino] was prepared by hydrolysis of 4-[3-glutarimido-2,4,6-triiodo-5-(N-methylacetamido)benzoyl]morpholine (Example 50, part b) with dilute sodium hydroxide according to the procedure of Example 10, and was obtained as a colorless solid, m.p. 281°–284° C. (dec.) when recrystallized from acetic acid.

By replacing the 4-[3-glutarimido-2,4,6-triiodo-5-(N-methylacetamido)benzoyl]morpholine by 1-[3-glutarimido-2,4,6-triiodo-5-(N-methylacetamido)benzoyl]piperidine or 1-[3-glutarimido-2,4,6-triiodo-5-(N-methylacetamido)benzoyl]pyrrolidine there can be obtained, respectively, 2',4',6'-triiodo-3'-(N-methylacetamido)-5'-(piperidinocarbonyl)glutaranilic acid [B; R is $CH_3CON(CH_3)$, R' and R" are H, Y' is $CH_2CH_2CH_2$, Z is piperidino] or 2',4',6'-triiodo-3'-(N-methylacetamido)-5'-(pyrrolidinocarbonyl)-glutaranilic acid [B; R is $CH_3CON(CH_3)$, R' and R" are H, Y' is $CH_2CH_2CH_2$, Z is pyrrolidino].

EXAMPLE 52

2',4',6'-Triiodo-3'-(N-methylacetamido)-5'-(morpholinocarbonyl)-N-methylglutaranilic Acid [B; R is $CH_3CON(CH_3)$, R' is $CH_3$, R" is H, Y' is $CH_2CH_2CH_2$, Z is morpholino] was prepared by methylation of 2',-

4',6'-triiodo-3'-(N-methylacetamido)-5'-(morpholinocarbonyl)glutaranilic acid (Example 51) with dimethyl sulfate according to the procedure of Example 24, and was obtained in the form of colorless crystals, m.p. 251°–257° C.

EXAMPLE 53

3,5-bis(Glutarimido)-2,4,6-triiodo-N-methylbenzamide [A; R is glutarimido, Y is $CH_2CH_2CH_2$, Z is $NHCH_3$] was prepared from the acid chloride of 3,5-bis(glutarimido)-2,4,6-triiodobenzoic acid (from the compound of Example 4 and thionyl chloride) and aqueous methylamine solution according to the procedure described in Example 45, part (a), and was obtained in the form of pale tan prisms, m.p. 271°–272° C. (dec.) when recrystallized from acetic acid.

EXAMPLE 54

N,N'-[2,4,6-Triiodo-5-(methylcarbamoyl)-m-phenylene]bis(glutaramic Acid) [B; R is $HOOC(CH_2)_3CONH$, R' and R" are H, Y' is $CH_2CH_2CH_2$, Z is $NHCH_3$] was prepared by hydrolysis of 3,5-bis-(glutarimido)-2,4,6-triido-N-methylbenzamide (Example 53) with ethanolic sodium hydroxide, ten minutes at 100° C., and was obtained in the form of colorless crystals, m.p. 269°–270° C. (dec.) when recrystallized from aqueous dimethylformamide.

EXAMPLE 55

3,5-bis(Glutarimido)-2,4,6-triiodo-N,N-dimethylbenzamide [A; R is glutarimido, Y is $CH_2CH_2CH_2$, Z is $N(CH_3)_2$] was prepared from the acid chloride of 3,5-bis(glutarimido)-2,4,6-triiodobenzoic acid (Example 4) and aqueous dimethylamine according to the procedure of Example 45, part (a), and was obtained in the form of colorless crystals, m.p. above 340° C. when recrystallized from acetonitrile.

EXAMPLE 56

N,N'[2,4,6-Triiodo-5-(dimethylcarbamoyl)-m-phenylene]bis(glutaramic Acid) [B; R is $HOOC(CH_2)_3CONH$, R' and R" are H, Y' is $CH_2CH_2CH_2$, Z is $N(CH_3)_2$] was prepared by hydrolysis of 3,5-bis(-glutarimido)-2,4,6-triiodo-N,N-dimethylbenzamide (Example 55) with sodium hydroxide, and was obtained as a colorless solid, m.p. 244°–246° C.

EXAMPLE 57

3,5-bis(Succinimido)-2,4,6-triiodobenzoic Acid [A; R is succinimido, Y is $CH_2CH_2CH_2$, Z is OH] was prepared from 50 g. of 3,5-diacetamido-2,4,6-triiodobenzoic acid and 150 g. of succinic anhydride in the presence of 5 ml. of concentrated sulfuric acid, 30 minutes at 134° C., and was obtained in the form of pale cream crystals, m.p. above 300° C. when recrystallized from acetic acid.

EXAMPLE 58

N,N'(5-Carboxy-2,4,6-triiodo-m-phenylene)disuccinamic Acid [B; R is $HOOCCH_2CH_2CONH$, R' and R" are H, Y' is $CH_2CH_2$, Z is OH] was prepared by hydrolysis of 3,5-bis(succinimido)-2,4,6-triiodobenzoic acid (Example 57) with dilute sodium hydroxide, and was obtained in the form of pale tan crystals, m.p. 229°–230° C. (dec.) when recrystallized from acetic acid.

EXAMPLE 59 a. 3-Nitro-5-(3,6,9-trioxadecanamido)benzoic Acid [G'; T is $CH_3OCH_2CH_2OCH_2CH_2OCH_2$, Z is OH].

A mixture of 14.6 g. of 3-amino-5-nitrobenzoic acid and 17.1 g. of 3,6,9-trioxadecanoic acid chloride in 200 ml. of dioxane was heated at reflux for 24 hours. The reaction mixture was concentrated to remove the solvent. The residue was dissolved in dilute sodium hyroxide and then acidifed with hydrochloric acid. The resulting product (13.6 g., m.p. 130° C.) was recrystallized from acetonitrile to give 3-nitro-5-(3,6,9-trioxadecanamido)benzoic acid as a beige solid, m.p. 136°–137° C.

b. 3-Amino-5-(3,6,9-trioxadecanamido)benzoic Acid [H; T is $CH_3OCH_2CH_2OCH_2CH_2OCH_2$, Z is OH] was prepared by hydrogenation of 80 g. of 3-nitro-5-(3,6,9-trioxadecanamido)benzoic acid in absolute ethanol in the presence of palladium-on-charcoal catalyst. There was thus obtained 54.7 g. of 3-amino-5-(3,6,9-trioxadecanamido)benzoic acid, m.p. 130.5°–131° C. when recrystallized from isopropyl alcohol.

c. 3-Amino-2,4,6-triiodo-5-(3,6,9-trioxadecanamido)benzoic Acid [J; T is $CH_3OCH_2CH_2OCH_2CH_2OCH_2$, Z is OH] was prepared by iodination of 3-amino-5-(3,6,9-trioxadecanamido)benzoic acid with sodium iododichloride according to the procedure of Example 20, part (d), and was obtained in the form of a tan solid, m.p. 177°–178° C. when recrystallized from methanol and a methanol-benzene mixture.

d. 3-Amino-2,4,6-trioodo5-(N-methyl-3,6,9-trioxadecanamido)benzoic Acid [C; R° is $H(CH_2OCH_2)_3CON(CH_3)$, Q is H, Z is OH] was prepared by methylation of 3-amino-2,4,6-triiodo-5-(3,6,9-trioxadecanamido)benzoic acid with dimethyl sulfate according to the procedure of Example 41, and was obtained as an amorphous pink solid, m.p. 100°–109° C. when recrystallized from methanol.

EXAMPLE 60 a. 3-Cyclopropylcarboxamido-5-nitrobenzoic Acid [G'; T is cyclopropyl, Z is OH].

Cyclopropanecarboxylic acid chloride (57.5 g.) was added over a two minute period to a solution of 91 g. of 3-amino-5-nitrobenzoic acid in dioxane at 70° C. The reaction mixture was refluxed for about sixteen hours and the product isolated to give 89 g. of 3-cyclopropylcarboxamido-5-nitrobenzoic acid, m.p. 266°–266.5° C.

b. 3-Cyclopropylcarboxamido-5-aminobenzoic Acid [H; T is cyclopropyl, Z is OH].

A solution prepared from 89.5 g. of 3-cyclopropylcarboxamido-5-nitrobenzoic acid and 142 ml. of 2.5N sodium hydroxide was hydrogenated in the presence of 3 g. of 10% palladium-on-carbon catalyst. The catalyst was removed by filtration and the filtrate acidified. The product was collected and dried to give 62.5 g. of 3-cyclopropylcarboxamido5-aminobenzoic acid.

c. 3-Amino-5-(cyclopropylcarboxamido)-2,4,6-triiodobenzoic Acid [J; T is cyclopropyl, Z is OH].

To a solution of 62.1 g. of 3-cyclopropylcarboxamido5-nitrobenzoic acid and 95 ml. of 3N hydrochloric acid in 750 ml. of water was added 330.5 ml. of 2.837N aqueous sodium iododichloride solution over a period of 27 minutes. The reaction mixture was heated at about 100° C. for several days. and the product was isolated and recrystallized from an isopropyl alcohol-methanol mixture to give 3-amino-5-(cyclopropylcarboxamido)-2,4,6-triiodobenzoic acid, light tan solid, m.p. 224° C. (dec.).

d. 3-Amino-5-(N-methylcyclopropylcarboxamido)-2,4,6-triiodobenzoic Acid [C; R° is cyclopropyl-CON(CH₃), Q is H, Z is OH].

A solution of 59.8 g. of 3-amino-5-(cyclopropylcarboxamido)-2,4,6-triiodobenzoic acid in 320 ml. of 10% sodium hydroxide solution was treated with 25.2 g. of dimethyl sulfate in 50 ml. of acetone. The product was isolated and purified by conversion to the sodium salt and back to the free acid, and by recrystallization from isopropyl alcohol, to give 3-amino-5-(N-methylcyclopropylcarboxamido)-2,4,6-triiodobenzoic acid, colorless solid, m.p. 268°–271° C.(dec.).

e. 3-Glutarimido-5-(N-methylcyclopropylcarboxamido)-2,4,6-triiodobenzoic Acid [A; R is cyclopropyl-CON(CH₃), Y is CH₂CH₂CH₂, Z is OH] can be prepared by interacting 3-amino-5-(N-methylcyclopropylcarboxamido)-2,4,6-triiodobenzoic acid with glutaric anhydride according to the procedure of Example 1.

f. 3'-Carboxy-5'-(N-methylcyclopropylcarboxamido)-2',4',6'-triiodoglutaranilic Acid [B; R is cyclopropyl-CON(CH₃), R' and R" are H, Y' is CH₂CH₂CH₂, Z is OH] can be prepared by hydrolyzing 3-glutarimido-5-(N-methylcyclopropylcarboxamido)-2,4,6-triiodobenzoic acid with dilute sodium hydroxide.

According to the foregoing procedures, cyclohexanecarboxylic acid chloride can be caused to react with 3-amino-5-nitrobenzoic acid and the resulting 3-cyclohexylcarboxamido-5-nitrobenzoic acid converted successively to 3-cyclohexylcarboxamino-5-aminobenzoic acid, 3-amino-5-(cyclohexylcarboxamido)-2,4,6-triiodobenzoic acid, 3-amino-5-(N-methylcyclohexylcarboxamido)-2,4,6-triiodobenzoic acid, 3-glutarimido-5-(N-methylcyclohexylcarboxamido)-2,4,6-triiodobenzoic acid [A; R is cyclohexyl CON(CH₃), Y is CH₂CH₂CH₂, Z is OH] and 3'-carboxy-5'-(N-methylcyclohexylcarboxamido)-2',4',6'-triiodogulataranilic acid [B; R is cyclohexyl CON(CH₃), R' and R" are H, Y' is CH₂CH₂CH₂, Z is OH].

EXAMPLE 61 a. 3,5-Di(siccinimido)-2,4,6-triido-N,N-dimethylbenzamide [A; R is succinimido, Y is CH₂CH₂, Z is N(CH₃)₂], yellow prisms, m.p. above 330° C., was prepared by reacting 3,5-di(succinimido)2,4,6-triiodobenzoic acid (Example 57) with thionyl choride and then with aqueous dimethylamine.

b) N,N'-(Dimethylcarbamoyl)-2,4,6-triiodo-m-phenylene]bis-[succinamic acid] [B; R is HOOC(CH₂)₂CONH, R' and R" are H, Y' is CH₂CH₂, Z is N(CH₃)₂], colorless crystals, m.p. 228°–230° C. (decompn.), was prepared by mild alkaline hydrolysis of 3,5-di(succinimido)-2,4,6-triiodo-N,N-dimethylbenzamide.

EXAMPLE 62

3-{3-[(2-Carboxyethyl)sulfonyl]propionamido}-2,4,6-triiodo-5-(N-methylacetamido)benzoic Acid [B; R is CH₃CON(CH₃), R' and R" are H, Y' is CH₂CH₂SO₂CH₂CH₂, Z is OH].

To a solution of 29.54 g. of 3-[3-(2-carboxyethylthio)propionamido]2,4,6-triido-5-(N-methylacetamido)benzoic acid (Example 37) in 175 ml. of glacial acetic acid at room temperature was added in portions 8.69 g. of an aqueous solution containing 2.695 g. of hydrogen peroxide. The mixture was heated on a steam bath for one hour, and then concentrated in vacuo to remove the solvents. The residue was dissolved in aqueous sodium hydroxide, decolorized with activated charcoal and reprecipitated with hydrochloric acid. The product was collected and dried to give 17.75 g. of 3-{3-[(2-carboxyethyl)sulfonyl]propionamido}-2,4,6-triiodo-5-(N-methylacetamido)benzoic acid, light beige amorphous solid, m.p. 234°–241° C. (decompn.).

EXAMPLE 63 a. 2,4,6-Triiodo-3-{3-[2-(methoxycarbonyl)ethylthio]propionamido}-5-(N-methylacetamido)benzoic Acid [B; R is CH₃CON(C₂H₅), R' is H, R" is CH₃, Y' is CH₂CH₂SCH₂CH₂, Z is OH], colorless powder, m.p. 152°–170° C., was prepared from 3-amino-5-(N-ethylacetamido)-2,4,6-triiodobenzoic acid and ClCOCH₂CH₂SCH₂CH₂COOCH₃ according to the procedure of Example 36.

b. 3-[3-(2-Carboxyethylthio)propionamido]-2,4,6-triiodo-5-(N-ethylacetamido)benzoic Acid [B; R is CH₃CON(C₂H₅), R' and R" are H, Y' is CH₂CH₂SCH₂CH₂, Z is OH], colorless powder, m.p. 190°–199° C., was prepared by alkaline hydrolysis of 2,4,6-triido-3-{3-[2-(methoxycarbonyl)ethylthio]propionamido}-5-(N-ethylacetamido)benzoic acid according to the procedure of Example 37.

c. 3-[3-(2-Carboxyethylsulfonyl)propionamido]-2,4,6-triiodo-5-(N-ethylacetamido)benzoic Acid [B; R is CH₃CON(C₂H₅), R' and R" are H, Y' is CH₂CH₂SO₂CH₂CH₂, Z is OH] can be prepared by treating 3-[3-(2-carboxyethylthio)propionamido]-2,4,6-triiodo-5-(N-ethylacetamido)benzoic acid with hydrogen peroxide by the procedure described in Example 62.

I claim:

1. A compound of the formula

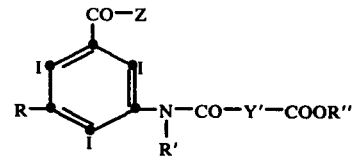

wherein Y' is a single bond, vinylene, or an alkylene bridge having from one to eight carbon atoms or such a group interrupted by from one to three members selected from O, S, SO and SO₂, said members, when more than one, being separated by at least two carbon atoms; Z is morpholino, pyrrolidino or piperidino; R is H₂N, HOOC—Y'—CO—NH, HOOC—Y'—CO—N(-lower alkyl), T—CO—NH, T—CO—NHCH₂, or (T—CO)N(lower alkyl, where T is hydrogen, cycloalkyl of 3–6 ring members, or alkyl of 1–8 carbon atoms optionally interrupted by from 1 to 4 oxygen atoms, each oxygen, when more than one, being separated by at least two carbon atoms; R' is hydrogen, lower-alkyl, hydroxy-lower-alkyl, lower-alkoxylower-alkyl, or lower-alkoxy-lower-alkoxy-lower-alkyl; and R" is hydrogen or lower-alkyl.

2. A compound according to claim 1 wherein R" is hydrogen and Z is morpholino.

3. A compound according to claim 1 wherein R" is hydrogen, Z is morpholino and R is (T—CO)N(lower-alkyl), T being alkyl of 1–8 carbon atoms.

4. 2',4',6'-Triiodo-3'-(N-methylacetamido)-5'-(morpholinocarbonyl)glutaranilic acid, according to claim 2.

5. 2',4',6'-Triido-3'-(N-methylacetamido)-5'-(morpholinocarbonyl)-N-methylglutaranilic acid, according to claim 2.

* * * * *

UNITED STATES PATENT AND TRADEMARK OFFICE
CERTIFICATE OF CORRECTION

PATENT NO. : 4,031,088
DATED : June 21, 1977
INVENTOR(S) : James H. Ackerman

It is certified that error appears in the above-identified patent and that said Letters Patent are hereby corrected as shown below:

Cover page, second column, "Thomas J. Johnson" should read --Thomas L. Johnson--.

Column 1, line 43, "O. S." should read --O, S,--.

Column 2, line 12, after "$-CH_2SO_2CH_2-$," insert -- $-CH(CH_3)OCH_2-$,--.

Column 26, line 50, Claim 1, "(lower alkyl," should read --(lower-alkyl),--; line 55, Claim 1, "-alkoxylower-" should read -- -alkoxy-lower- --; line 65, Claim 5, "Triido" should read --Triiodo--.

Signed and Sealed this

Fifteenth Day of November 1977

[SEAL]

Attest:

RUTH C. MASON
*Attesting Officer*

LUTRELLE F. PARKER
*Acting Commissioner of Patents and Trademarks*